United States Patent
Clark

(10) Patent No.: US 7,938,122 B2
(45) Date of Patent: May 10, 2011

(54) DEVICE AND METHOD FOR NIPPLE RECONSTRUCTION

(75) Inventor: Anthony L Clark, San Jose, CA (US)

(73) Assignee: Asteame Medical Devices Inc., Saratoga, CA (US)

( * ) Notice: Subject to any disclaimer, the term of this patent is extended or adjusted under 35 U.S.C. 154(b) by 53 days.

(21) Appl. No.: 12/098,188

(22) Filed: Apr. 4, 2008

(65) Prior Publication Data

US 2008/0188787 A1 Aug. 7, 2008

Related U.S. Application Data

(63) Continuation-in-part of application No. 11/254,760, filed on Oct. 21, 2005, now abandoned.

(60) Provisional application No. 60/628,158, filed on Nov. 17, 2004.

(51) Int. Cl.
*A61J 13/00* (2006.01)
*A61F 13/00* (2006.01)

(52) U.S. Cl. ............... 128/890; 602/41; 602/42; 602/61

(58) Field of Classification Search .................. 602/58, 602/61, 41–43; 128/888–890, 893, 894; 604/346; 623/8
See application file for complete search history.

(56) References Cited

U.S. PATENT DOCUMENTS

| | | | | |
|---|---|---|---|---|
| 3,063,555 A | * | 11/1962 | Hanington | 206/440 |
| 4,054,140 A | * | 10/1977 | Etes | 604/343 |
| 4,754,750 A | * | 7/1988 | Imonti | 128/890 |
| 4,870,977 A | * | 10/1989 | Imonti | 128/890 |
| 5,026,394 A | | 6/1991 | Baker | |
| 5,425,762 A | | 6/1995 | Muller | |
| 5,855,606 A | | 1/1999 | Eaton | |
| 5,997,574 A | | 12/1999 | Hayes et al. | |
| 6,468,295 B2 | * | 10/2002 | Augustine et al. | 607/96 |
| 2002/0029010 A1 | * | 3/2002 | Augustine et al. | 602/41 |
| 2003/0074084 A1 | | 4/2003 | Nakao | |

OTHER PUBLICATIONS

"Asteame (TM) Medical Devices Nipple Guard (TM)" Product Description (2 pgs.), Asteame FAQ, Asteame Medical Devices, Oct. 26, 2006.
"How does the nipple guard work?", Asteame FAQ, Asteame Medical Devices (web page at http://www.asteame.com/cust_care/ccfaq2.html (downloaded Oct. 16, 2009)), dated Aug. 2006.
"How the Nipple Guard (TM) Works," White Paper, Asteame Medical Devices, Aug. 9, 2006, 7 pgs.

(Continued)

*Primary Examiner* — Kim M Lewis
(74) *Attorney, Agent, or Firm* — Davidson Berquist Jackson & Gowdey, LLP; Brian Siritzky

(57) ABSTRACT

A nipple reconstruction device includes a core component having a substantially circular hollow opening therein for receiving a person's nipple; padding attached to a lower part of the core and substantially lining the lower part of the core and at least a portion of the hollow opening in the core, and an attaching component constructed and adapted to hold the device in place on the person's skin. The core may be a semi-rigid, pliable, high durometer material. The padding may be gauze, woven rayon cellulose, cotton, a cotton/polyester blend material; or a non-woven, one-sided medical tape. The attaching component may be an adhesive tape having a plurality of tabs for holding the device in place on the person's skin.

20 Claims, 17 Drawing Sheets

OTHER PUBLICATIONS

International Preliminary Report on Patentability mailed Jul. 24, 2008 in PCT/US2007/000546 [5 pgs.].

International Preliminary Report on Patentability mailed Oct. 4, 2007 in PCT/US05/40731 [5 pgs.].

International Search Report and Written Opinion mailed Aug. 30, 2007 in PCT/US05/40731.

International Search Report and Written Opinion mailed October 4, 2007 in International Application No. PCT/US2007/000546.

* cited by examiner

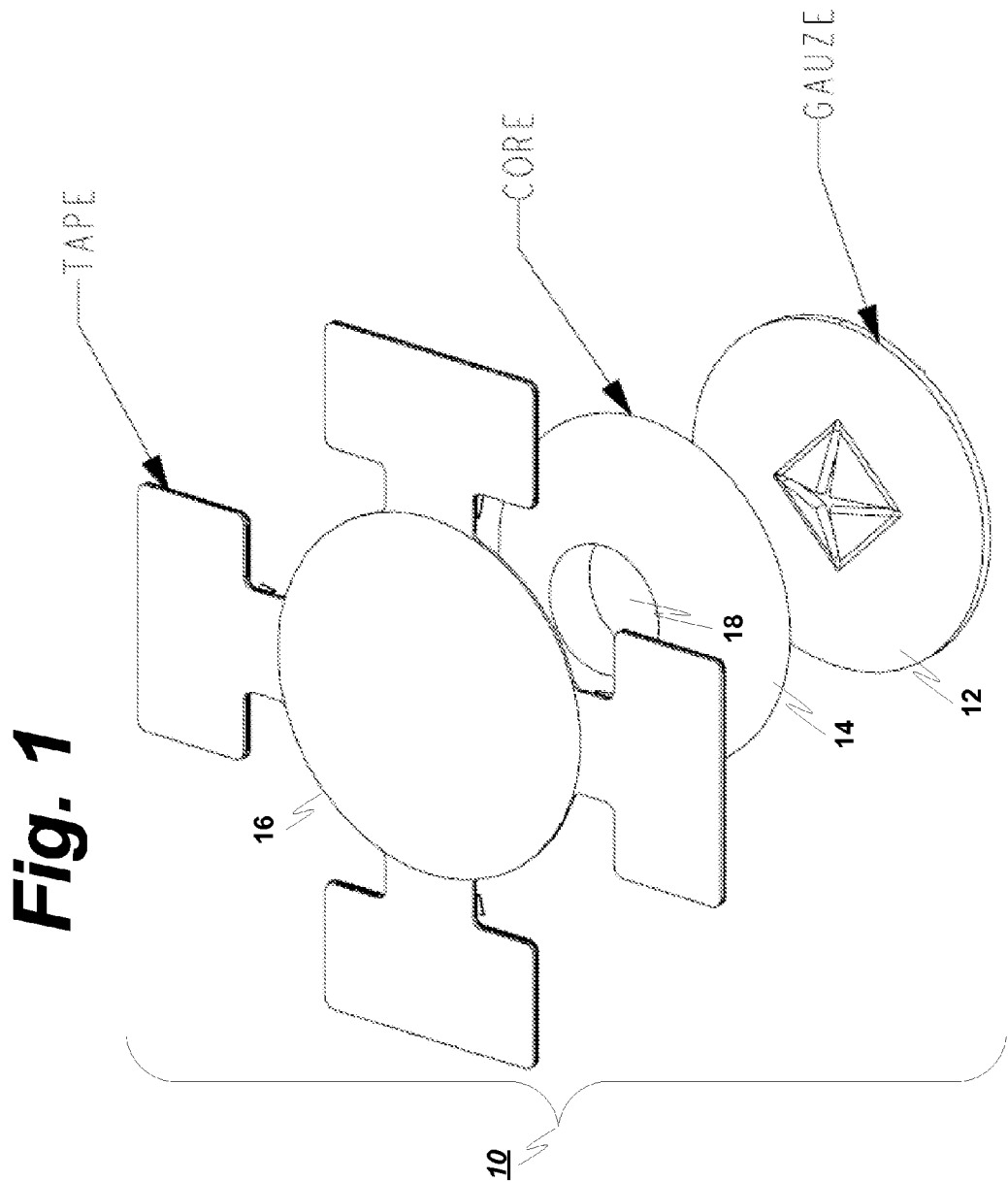

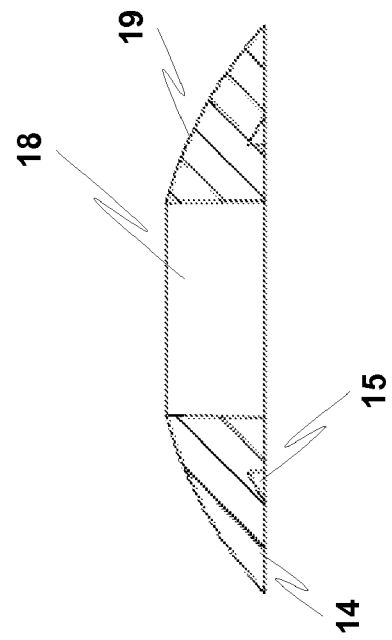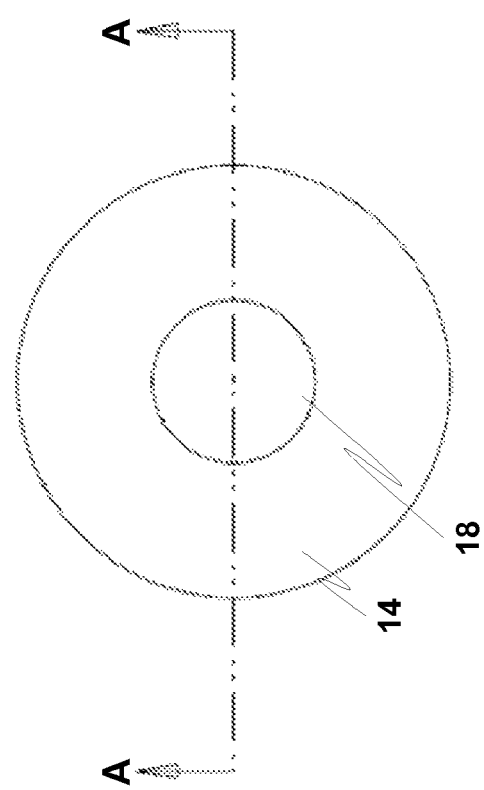

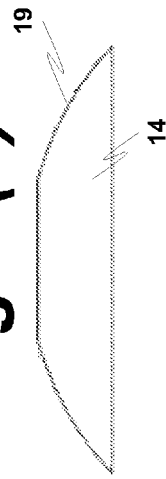
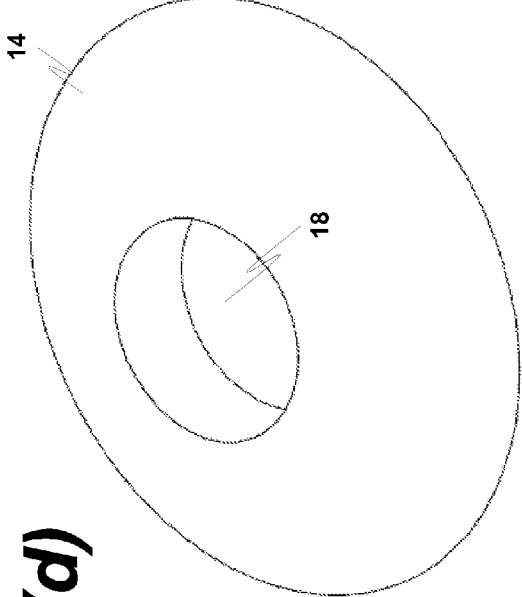
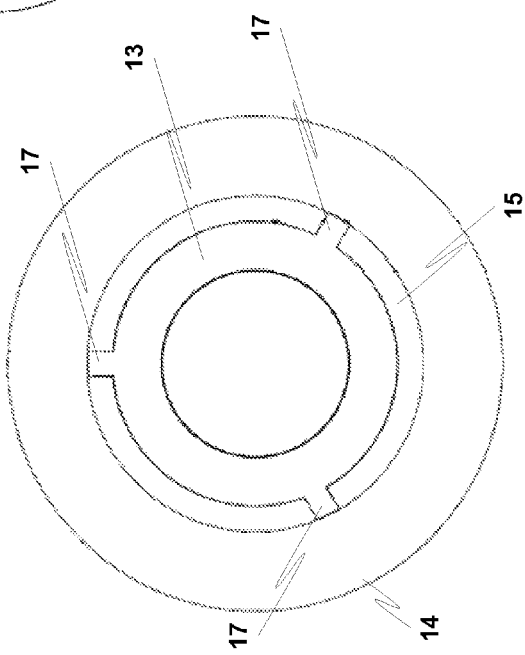

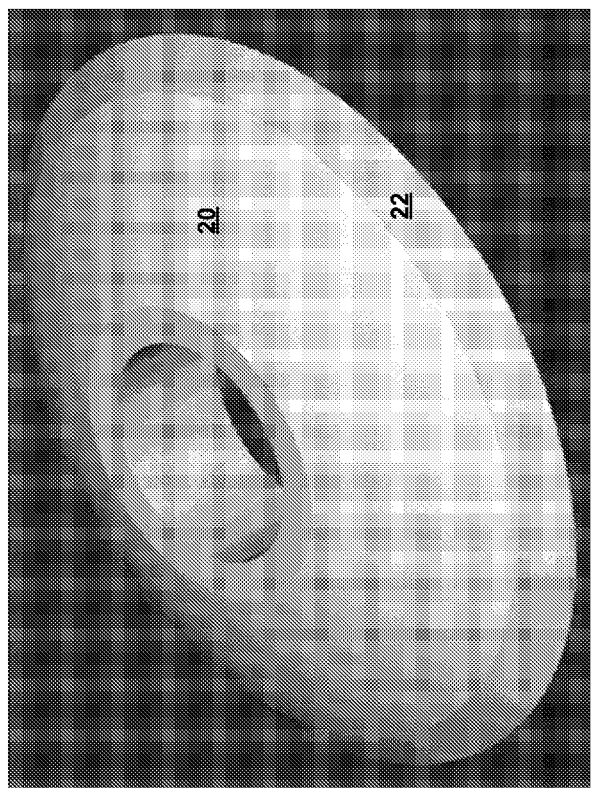
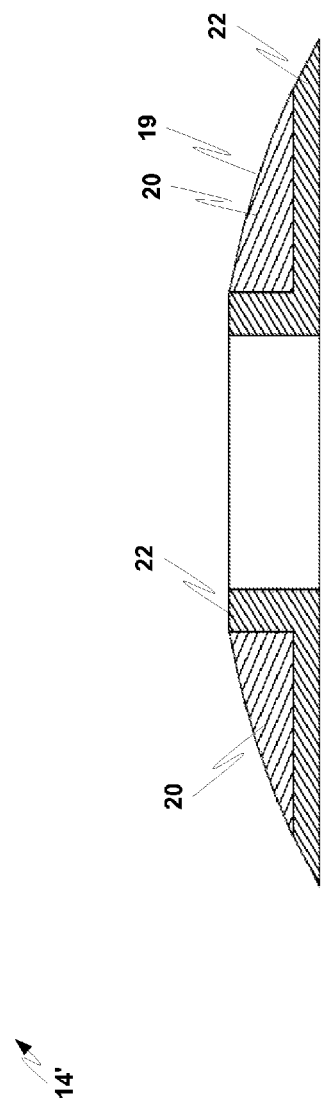
*Fig. 2(f)*
*Fig. 2(g)*

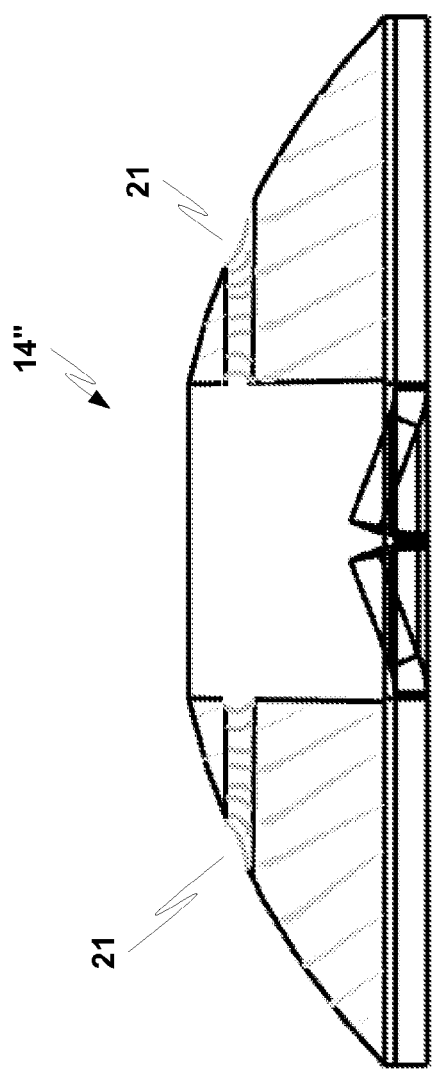
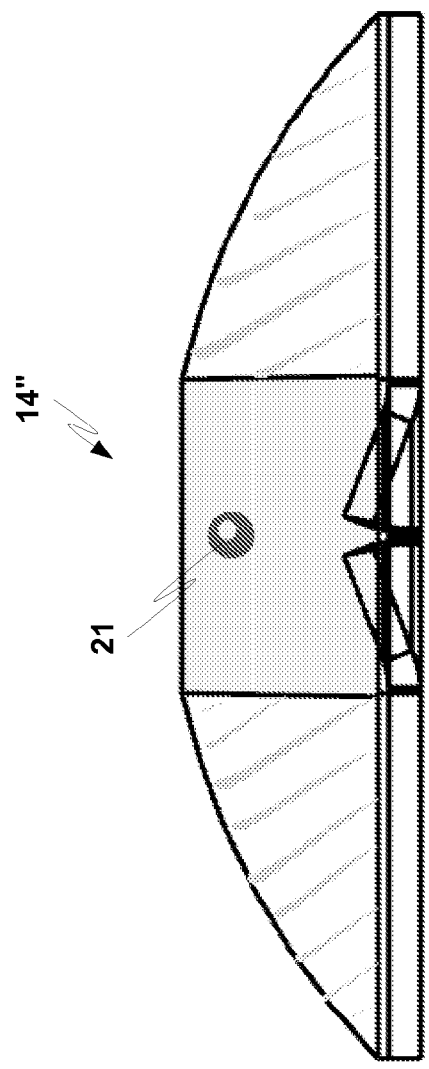
Fig. 2(h)
Fig. 2(i)

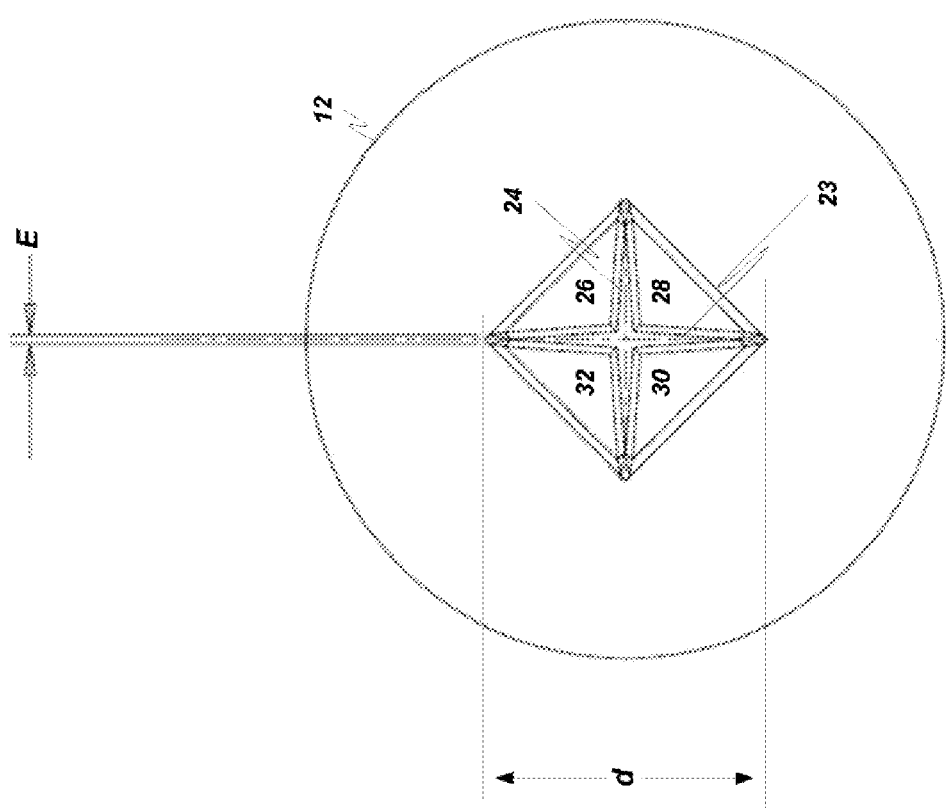

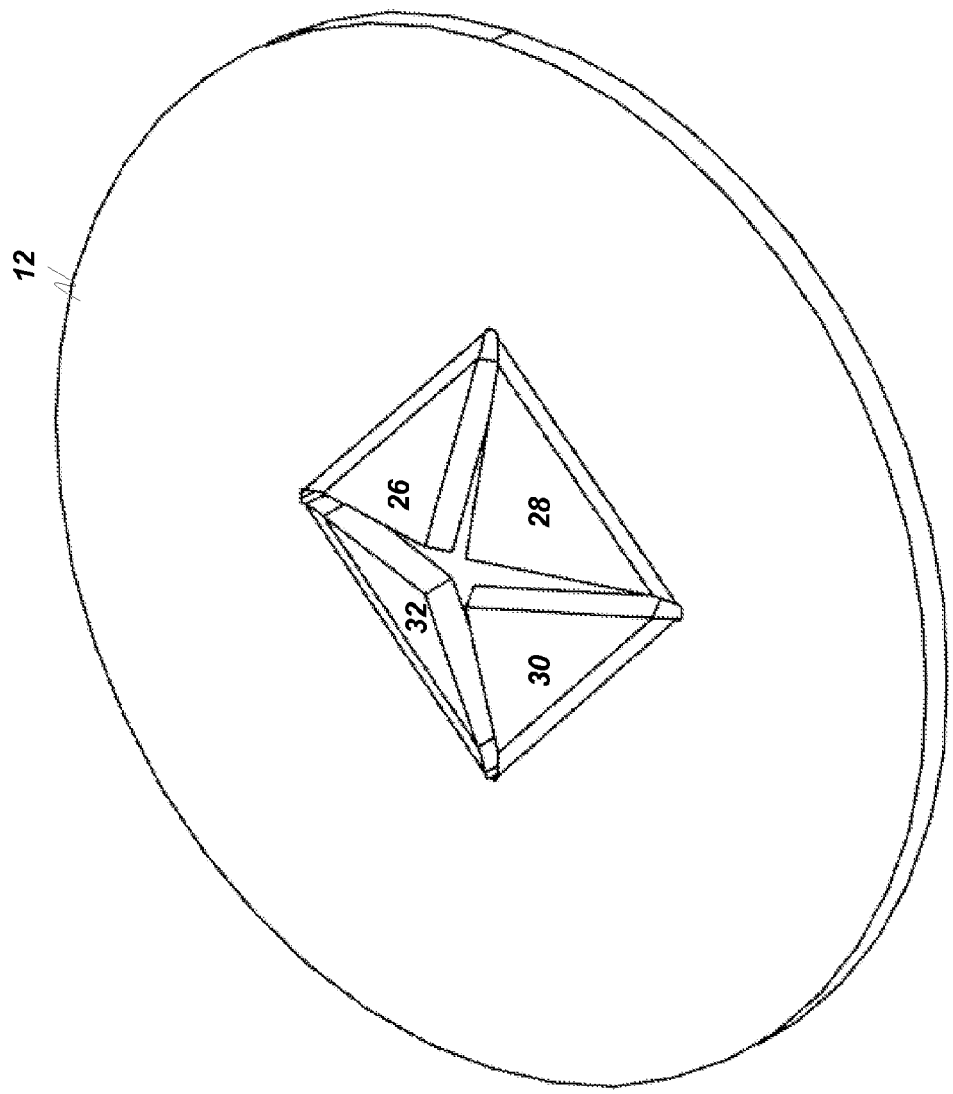
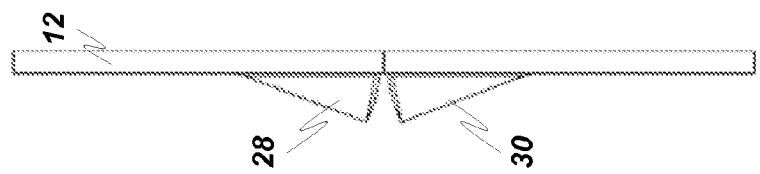
Fig. 3(b)
Fig. 3(c)

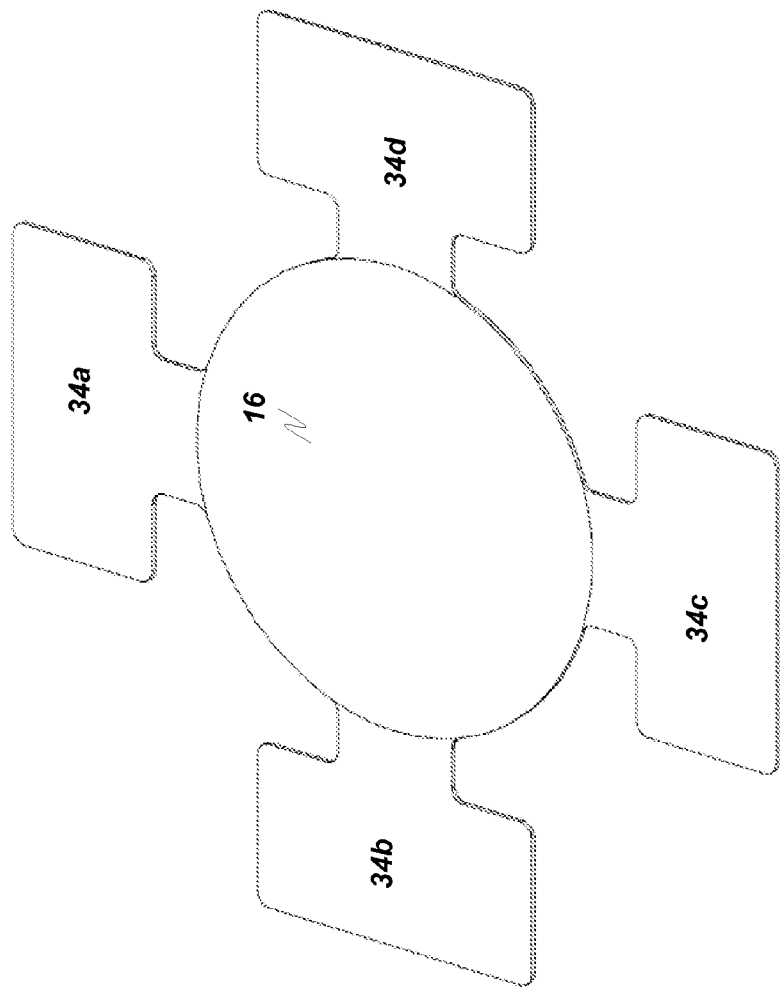
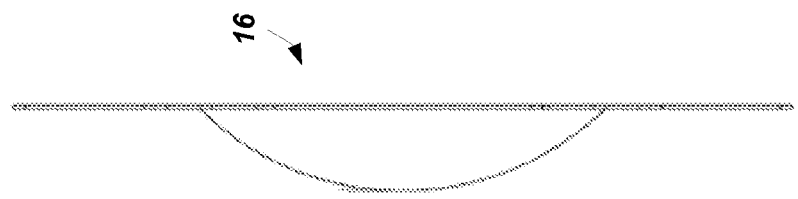

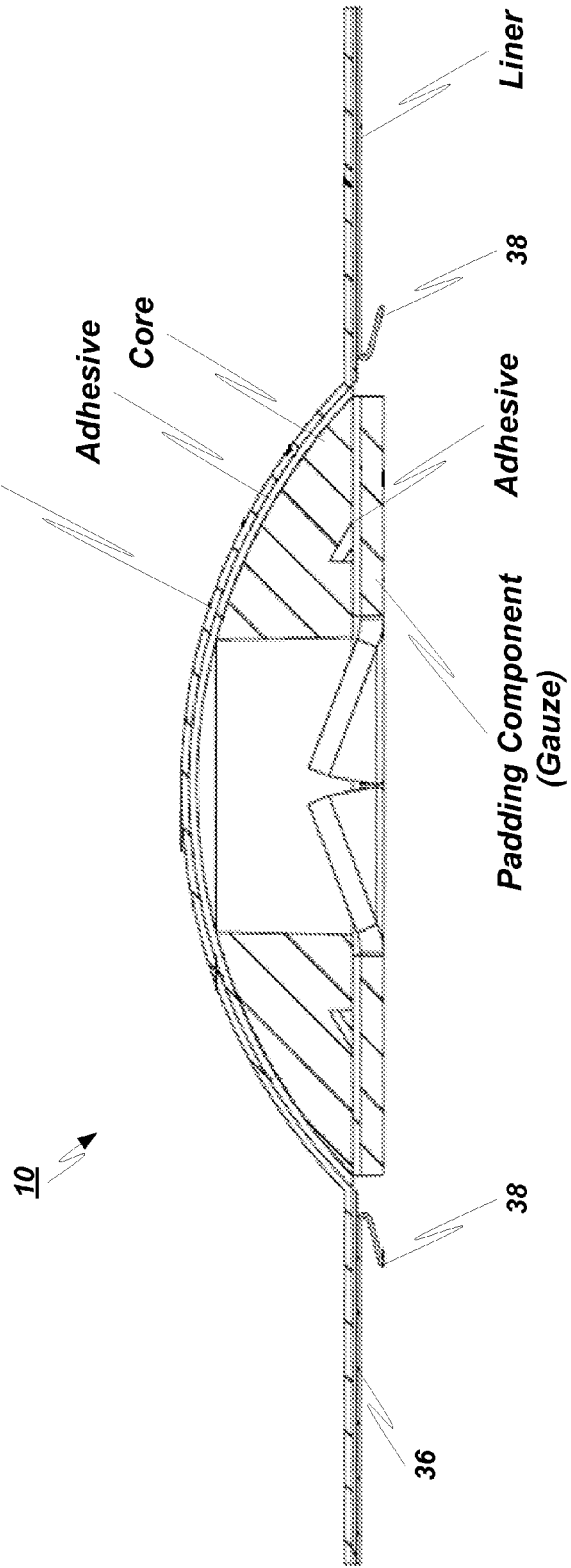

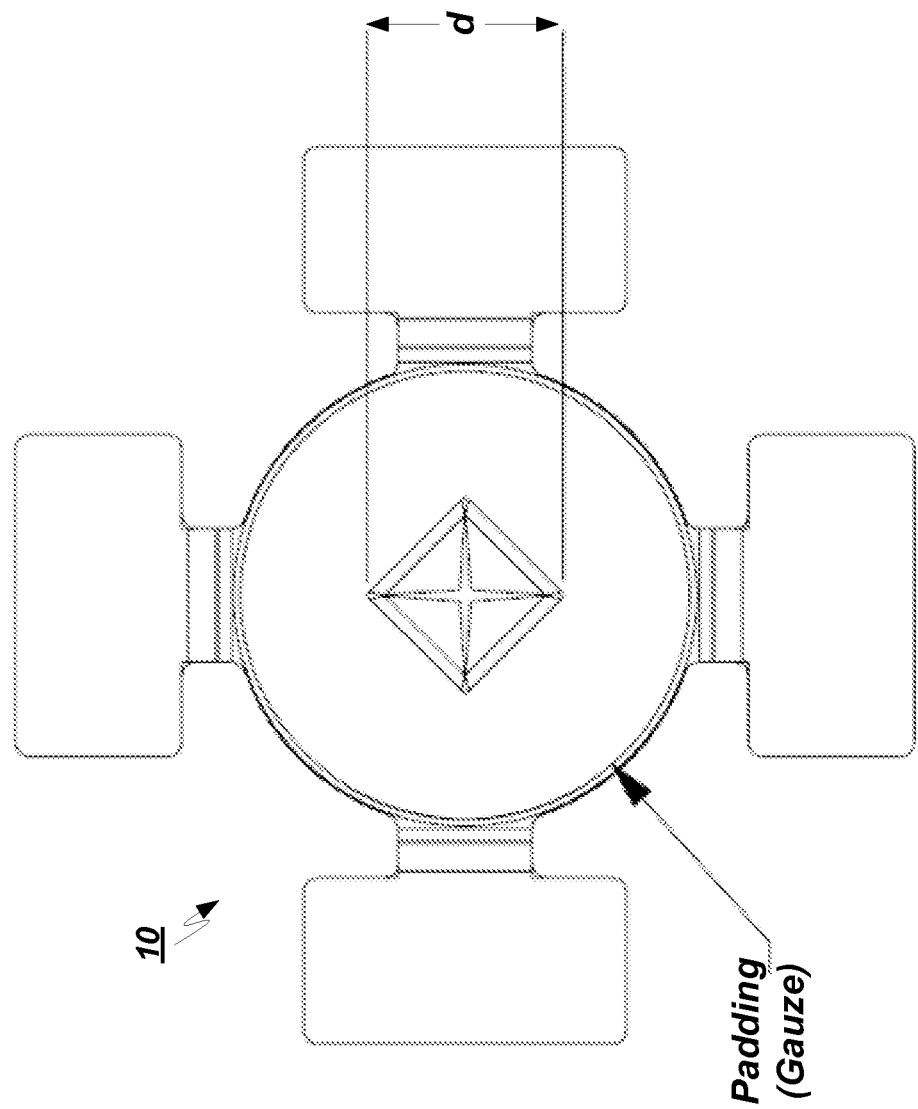

DEVICE AND METHOD FOR NIPPLE RECONSTRUCTION

RELATED APPLICATIONS

This application is a continuation-in-part of U.S. patent application Ser. No. 11/254,760, filed Oct. 21, 2005, titled "Nipple Reconstruction Device," the entire contents of which are incorporated herein for all purposes. application Ser. No. 11/254,760 is related to and claims priority from U.S. Provisional Application No. 60/628,158, titled "Cosmetic Nipple Reconstruction Guard," filed Nov. 17, 2004, the entire contents of which are incorporated herein by reference.

FIELD OF THE INVENTION

This invention relates to a nipple reconstruction device.

DETAILED DESCRIPTION OF THE PRESENTLY PREFERRED EXEMPLARY EMBODIMENTS

Detailed Description of the Drawings

Figure 3D:
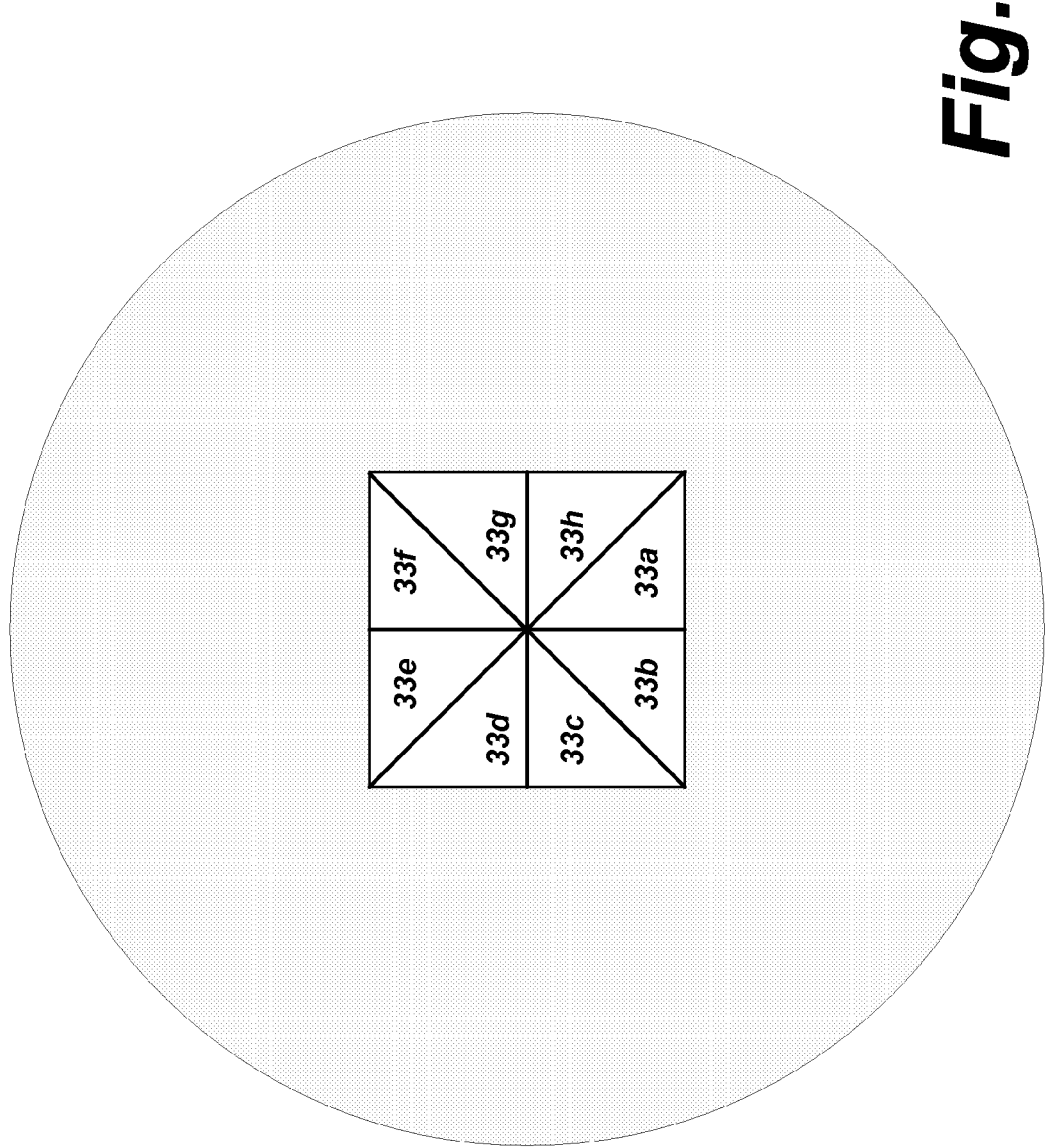
Figure 4A:
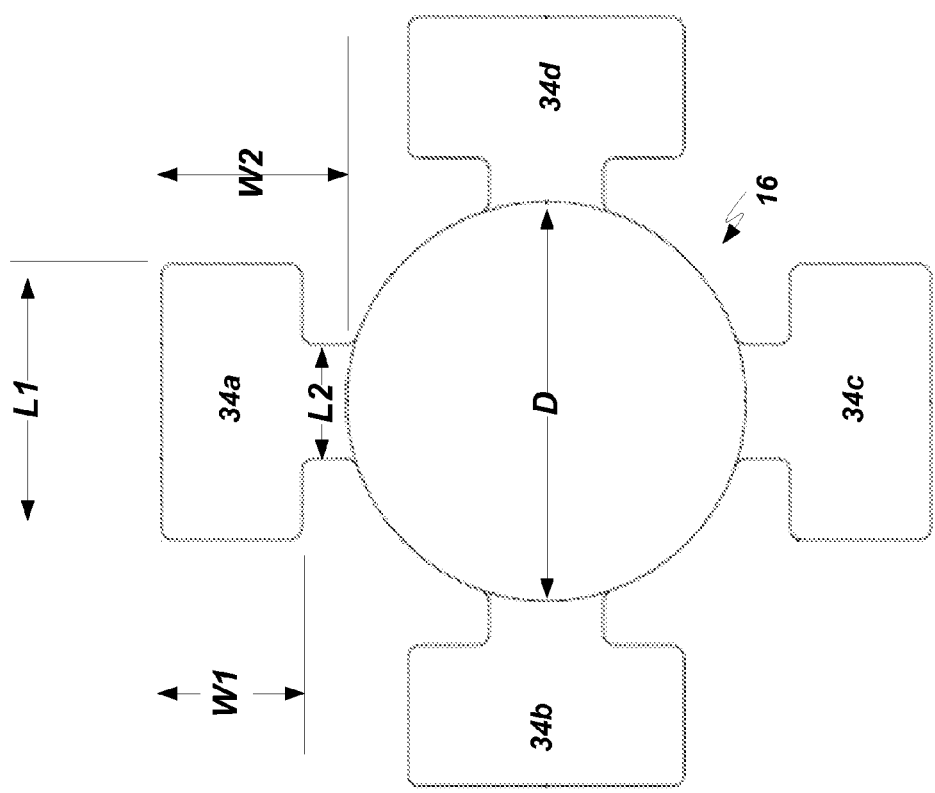
Figure 4E:
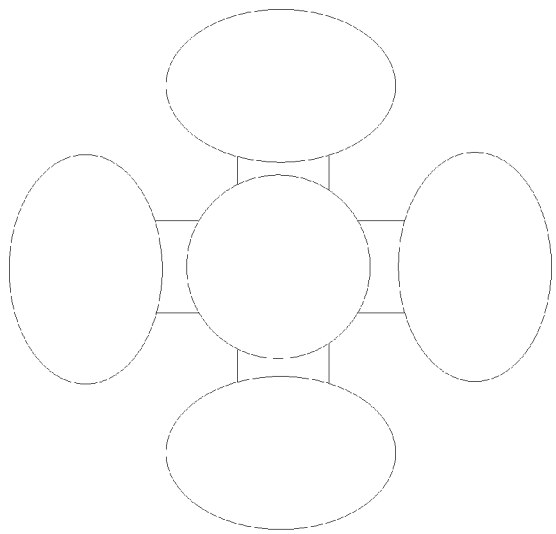
Figure 4F:
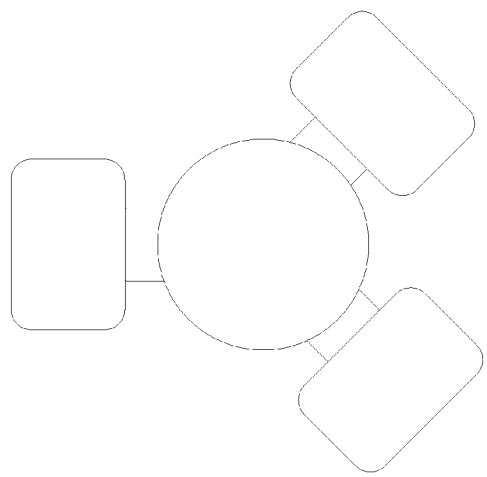
Figure 4D:
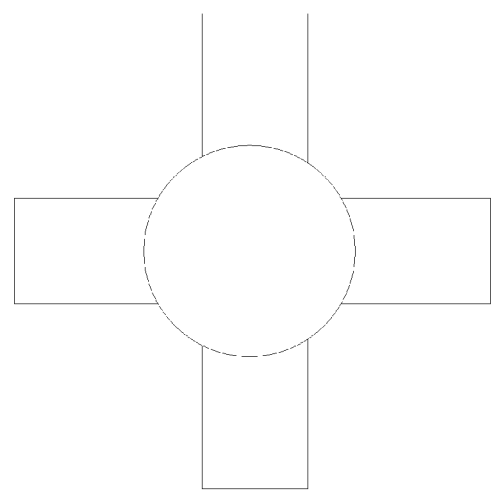
Figure 5A:
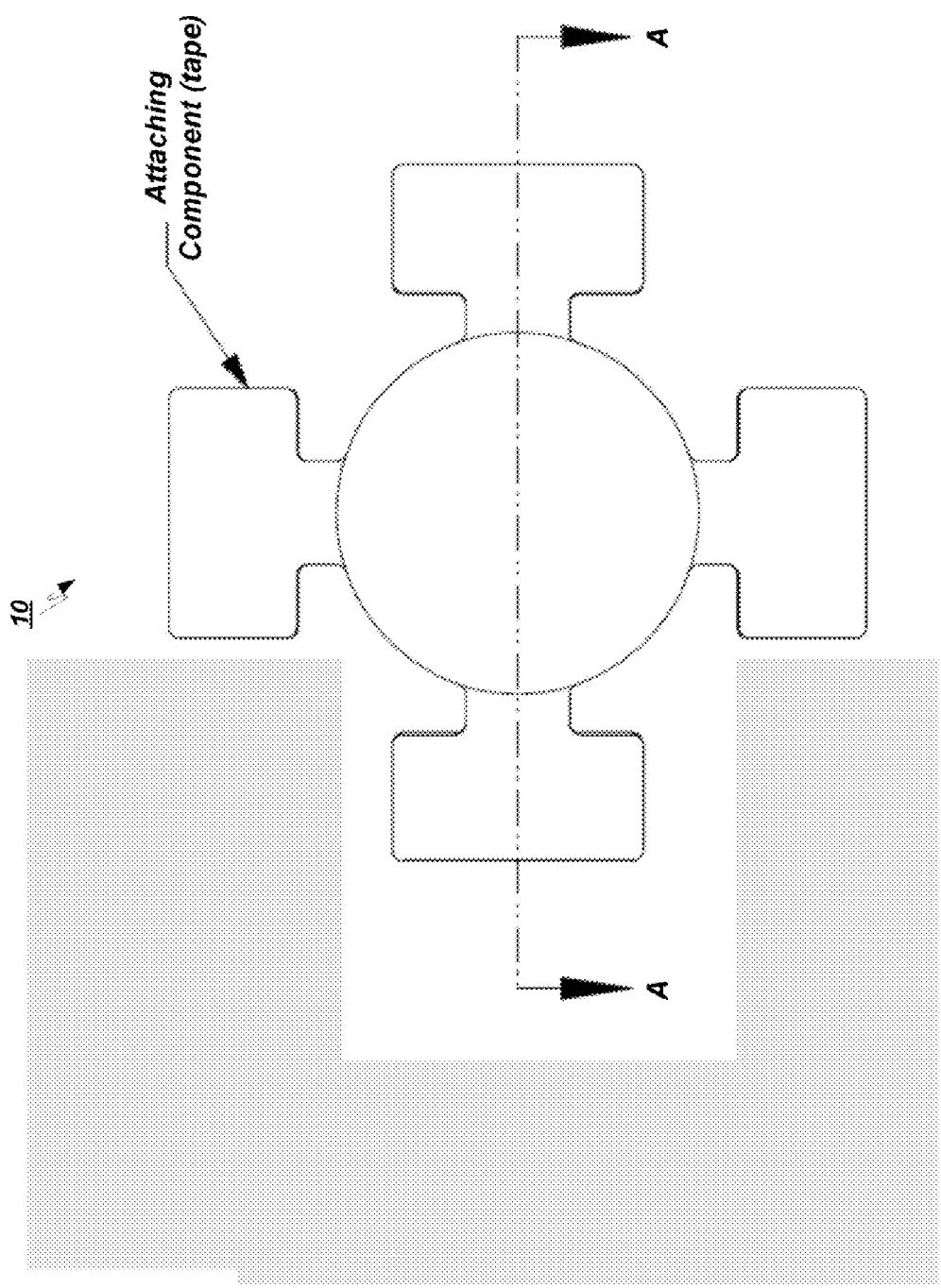
Figure 5B:
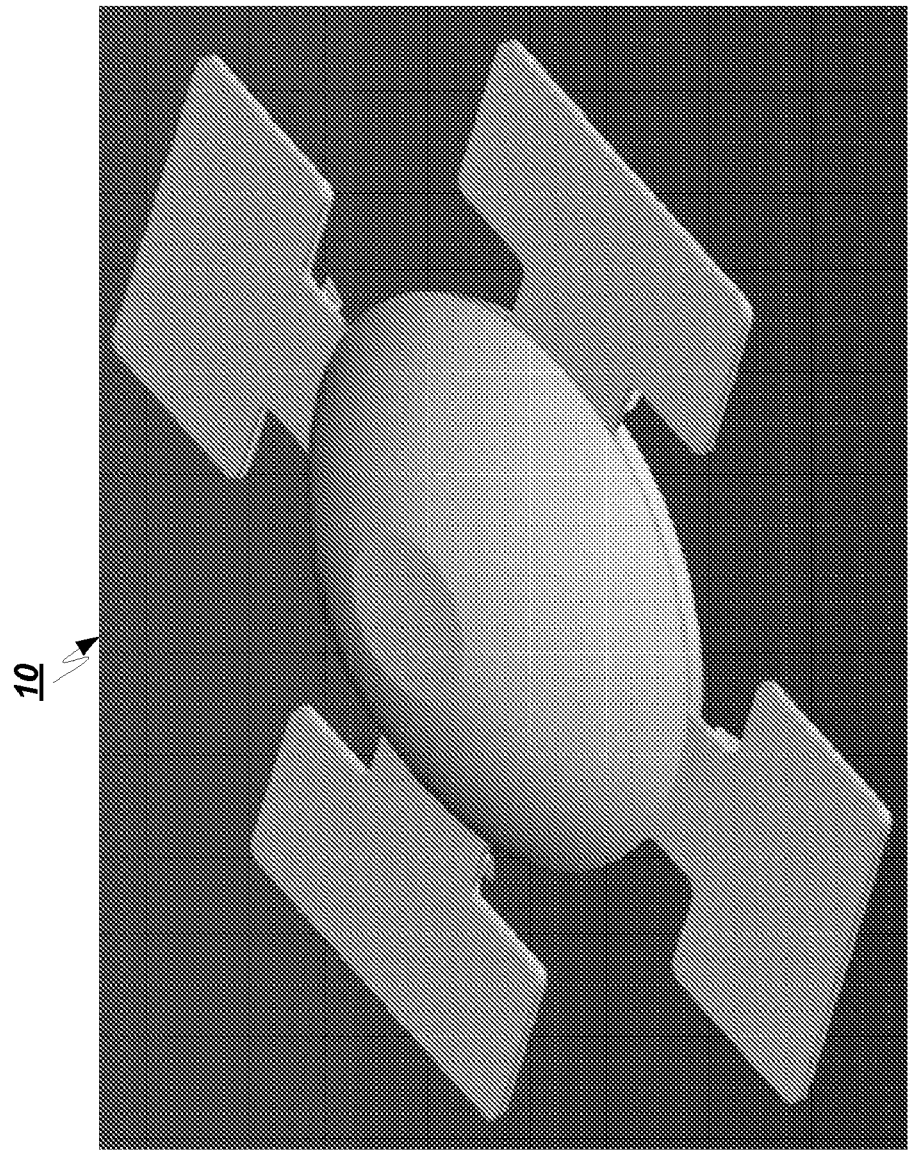
Figure 5E:
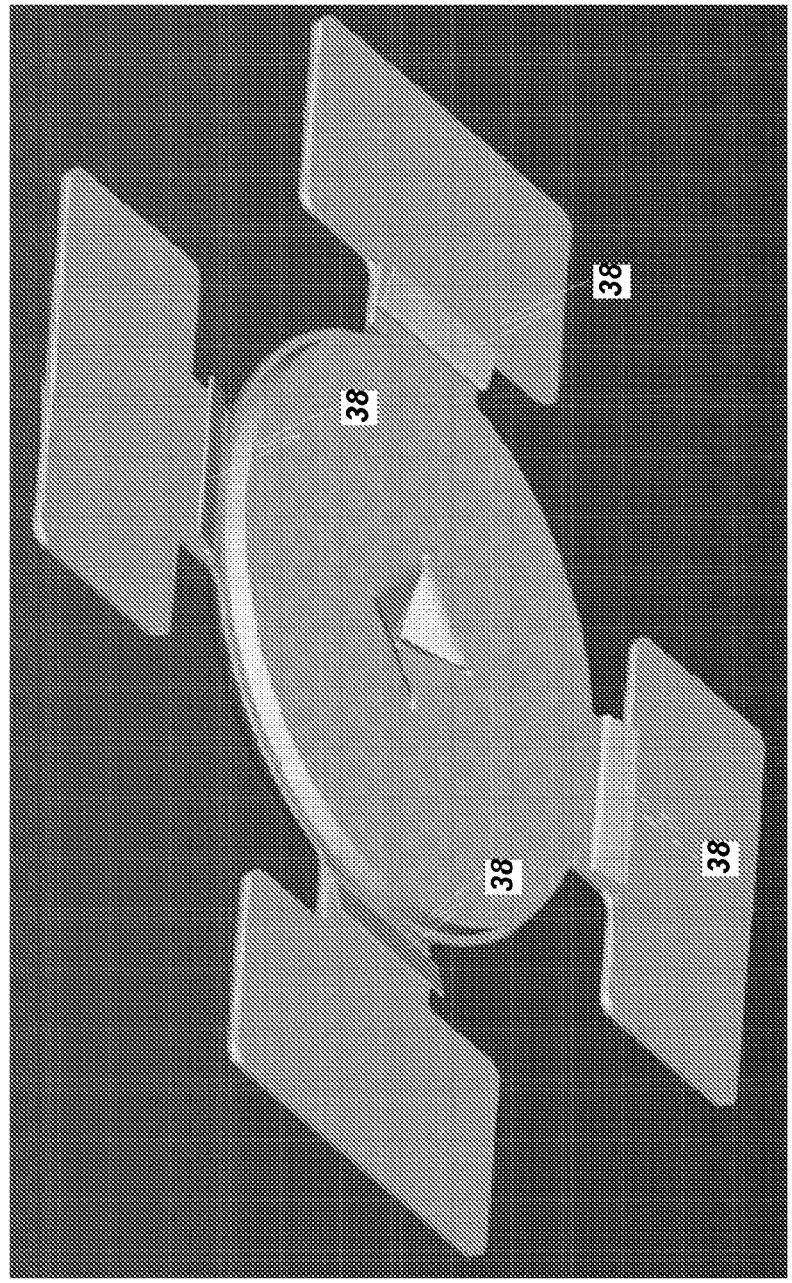
Figure 5F:
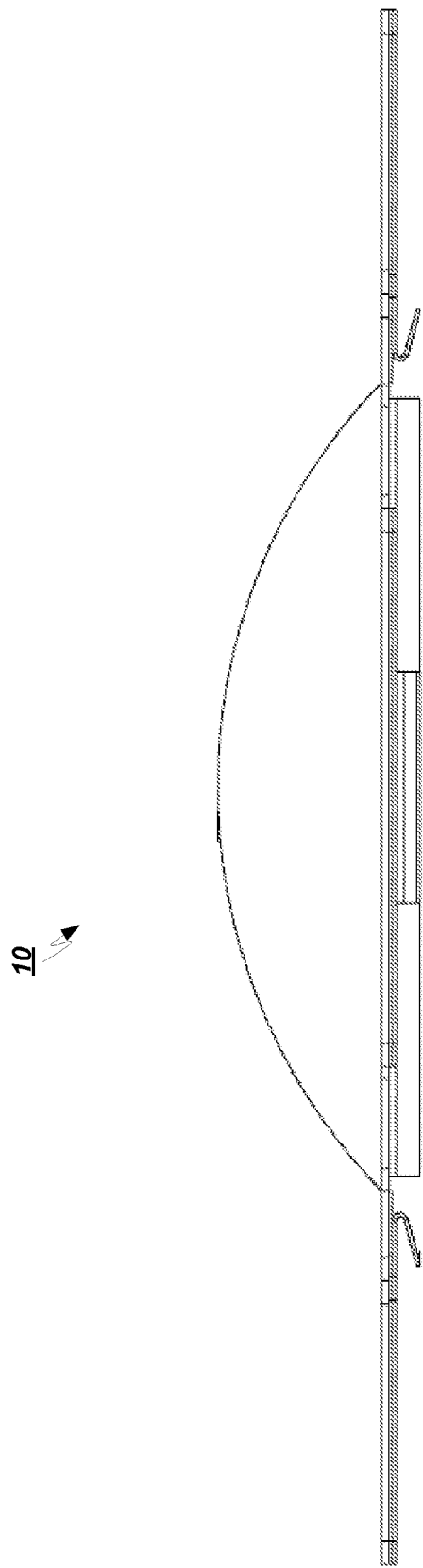

The invention is better understood by reading the following detailed description with reference to the accompanying drawings in which:

FIG. 1 shows an exploded view of a nipple reconstruction guard according to embodiments of the present invention;

FIGS. 2(a)-2(i) illustrate the core section of the device according to various embodiments of the present invention;

FIGS. 3(a)-3(c) are views of a padding section of the device according to embodiments of the present invention;

FIG. 3(d) shows an alternative cross cut of the padding section;

FIGS. 4(a)-4(f) show various views of the attaching component of nipple reconstruction guards according to embodiments of the present invention; and FIGS. 5(a)-5(f) provide various views of an assembled nipple reconstruction guard according to embodiments of the present invention.

BACKGROUND & SUMMARY

Nipple surgery may be performed on patients as a result of cancer treatment, trauma, or congenital abnormalities (such as an inverted nipple). Following a mastectomy procedure to treat breast cancer, nipple reconstruction surgery is most often done as the final stage of the breast reconstruction process.

Nipple reconstruction greatly increases the achievement of a realistic looking breast, and provides tangible psychological benefits to patients undergoing breast reconstruction. Nipple size, projection, position, shape, and color are key considerations in the reconstruction process. However, the achievement of a lasting aesthetic result can be an elusive goal.

Contemporarily, nipples are generally reconstructed from incised local flaps of skin and fat that are elevated from the breast mound to create a protrusion. The incised donor sites on the breast mound are typically closed by suturing the opposing skin edges together. Popular local skin flap procedures include the Skate Flap, S-Flap, and Star Flap.

Local skin flap procedures have generally replaced the use of (non-local) tissue grafts for nipple reconstruction. Tissue graft techniques that use tissue taken from the vaginal area or the ear lobe to construct the new nipple are no longer in favor due to the difficulty in preserving the blood supply to the transplanted tissue; which if compromised can lead to the death of the transplanted tissue.

Regardless of the specific nipple reconstruction technique that is used, size, projection, position, shape, and color are key considerations.

The post surgical recovery process for a newly constructed, or reconstructed nipple mirrors that of the wound healing process and is comprised of multiple stages that last several months to a couple of years. Table 1 provides a summary or overview of the entire wound (and reconstructed nipple) healing process.

TABLE 1

| Stage | Characteristics | Length |
|---|---|---|
| One | This stage often goes by the name of homeostasis and/or inflammatory phase. Clotting occurs and blood vessels are constricted to control bleeding in the wound. Inflammation occurs and is a visible indicator of the immune response. White blood cells clean the area of debris and bacteria. | Lasts several days: immediately after the wound is created to 2-5 days total. |
| Two | Known as the metabolic or proliferative phase. The body produces collagen to fill voids and to strengthen the wound. Stronger and thicker scars, than are ultimately needed, are produced. New blood vessels form. Wound edges pull together and moist areas are covered by a layer of skin. | Begins after stage one and lasts about 3 weeks. |
| Three | Generally goes by the name of maturation or remodeling phase. During this stage, the body refashions the scar and decides how much will remain. New collagen forms, which changes the shape of the wound and increases the tensile strength of tissue in the area. | Begins after stage two and lasts up to 2 years. |

Immediately following surgery, the reconstructed nipple is typically larger in size and has a more pronounced projection than it will ultimately have. This is mostly due to localized inflammation, the fact that the tissue has not yet tightened and scarred down, and the absence of compression forces on the nipple immediately following the surgical procedure.

One of ordinary skill in the art will recognize, upon reading this description, that the use of a local skin flap procedure, to create a new nipple, produces a larger contiguous wound that is comprised of the newly constructed nipple and the connected, sutured local donor skin site. In contrast, for tissue graft procedures, the tissue graft donor site area (e.g., typically the vaginal area or ear lobe) is distinct from the nipple site. For tissue graft procedures, the two wound sites heal independently of each another.

Despite a surgeon's technique and expertise with a particular local skin flap procedure, the created nipple will experience shrinkage and may even completely flatten. External compression forces on the nipple, such as from wearing a bra, and tensile, or pulling forces from scar tissue that forms within the local donor site area conspire to flatten the constructed nipple. It is common for the ultimate result to be a very small protrusion or no protrusion at all. One of ordinary skill in the art will readily observe that an effective treatment for nipple flattening must counteract the pulling forces on the newly created nipple that originate in the local skin flap donor site area and are characteristic of Stage Two and Stage Three of the healing process. Consequently, for local skin flap procedures the scope of an effective therapy to counter nipple flattening must cover Stage Two and Stage Three of the wound healing process summarized in Table 1.

Immediately following surgery, the common practice is for the nipple to be covered with antibiotic soaked gauze, and then is dressed with additional gauze that is cut in a donut shape and placed around it. The donut gauze is layered to the height of the nipple in an attempt to maintain the size, shape, and projection of the nipple. The distal tip of the nipple and surrounding gauze are then covered with more gauze and secured with either medical tape and/or a plastic waterproof cover. Some surgeons additionally cut off the end of a syringe and use it with layers of gauze to protect the nipple against external forces during the initial healing phase (i.e., Stage One of Table 1).

The post operative dressing remains on the patient for about three to five days, until the patient's follow-up, at which time the nipple is redressed in the same fashion except for the antibiotic soaked dressing. The patient is then instructed to change the dressing after showering for the following one to two weeks. During this phase of the recovery and healing time, the patient is typically instructed to not wear a compressive bra and to not undertake any activities where the stitches and integrity of the nipple could be compromised. Of course, specific protocols in regards to surgical procedure, dressing, and post-op care and instructions may vary with individual surgeons' technique and preferences.

One of ordinary skill in the art will recognize, upon reading this description, that while the use of layers of gauze and the use of prior art purpose-built surgical bandages, e.g., as described by Imonti in U.S. Pat. No. 4,754,750 and U.S. Pat. No. 4,870,977 (hereinafter "Imonti"), may be appropriate to protect a newly constructed nipple during Stage One and the very beginning of Stage Two of the healing process (see Table 1), these approaches do not adequately address the latter part of Stage Two and Stage Three of the healing process for nipples constructed using local skin flap procedures, wherein the action of the scar tissue within the donor site area pulls and flattens the nipple.

Neither the use of layers of gauze nor the use of the device described by Imonti does anything to counteract the pulling forces on the newly created nipple that originate in the local skin flap donor site area.

The surgical bandage defined in Imonti predates today's local skin flap procedures and full to anticipate the contribution of the pulling forces within the donor site area to nipple flattening. The Imonti surgical bandage is optimized for Stage One of the healing process for a newly constructed nipple and explicitly references nipples that are created from tissue grafts. For example, Imonti '977 states, at column 1, line 14, "Tissue is taken from the vaginal area or ear lobe to construct the nipple . . . "; and at column 1, line 62, "A further object of the present invention is to provide an improved bandage for the areola and nipple area which bandage is carefully configured so as to minimize contact with the reconstructed tissue of that area . . . " In describing the surgical bandage, Imonti confirms, at column 2, line 28 "A preferred design of the protector member has a generally flat upper surface. A large medication opening passes through the center of that surface is surrounded by a raised annular rim having a plurality of spaced suture holes through it. The raised wound, such as a reconstructed nipple, in the protector member can then be sutured through the suture holes so that it can stand up in the protector member without slumping down . . . " Further, column 4, line 59 of Imonti '977 again explicitly cites nipples that are constructed via a tissue graft procedure: "The newly-constructed nipple often tends to lean or sag during the healing process and so the present invention provides for circumferentially and radially spaced suture holes 64 in protector member 14'." One of ordinary skill in the art will recognize,  upon reading this description, that the process of nipple sagging which is characteristic of tissue graft nipple reconstruction procedures is distinct from the process of nipple flattening which is characteristic of local skin flap procedures.

A principal objective of the nipple reconstruction guard according to embodiments of the present invention is to overcome the limitations of prior art bandages by specifically counteracting the pulling forces on the newly created nipple that originate in the local skin flap donor site area during Stage Two and Stage Three of the healing process for a newly created nipple.

DESCRIPTION

FIG. 1 is an exploded view of a nipple reconstruction guard/device 10 according to embodiments of the present invention. As shown in FIG. 1, the nipple reconstruction guard 10 includes three main parts or sections, namely a padding section/component 12, a core section/component 14 and an attaching section/component 16, each of which is described in greater detail below.

In an assembled nipple reconstruction guard or device 10 according to embodiments of the present invention, the attaching section 16 covers the top of the device and has adhesive on the bottom surface of each of its four tabs which enables securing the entire device to a patient's skin. The core section 14 of the device 10 contains a hollow opening 18 that allows for the insertion of the reconstructed nipple. The padding section 12 covers the bottom of the device 10 and is positioned between the core section 14 of the device and a patient's skin.

The Core Section

FIGS. 2(a)-2(g) illustrate embodiments of a core section 14. FIG. 2(a) is a top view of a core section 14, and FIG. 2(b) provides a cross-sectional view of the core section 14 in FIG. 2(a), along the line denoted section A-A. FIGS. 2(c) and 2(d) are side and perspective views, respectively, of a core section 14 according to embodiments of the present invention. FIG. 2(e) is a bottom view of a core section 14 shown in FIG. 2(a).

The internal core section 14 of the device may be composed of rubber, synthetic rubber, polystyrene, foamed polystyrene, silicone, various other plastics, Styrofoam or combinations of these materials or any other semi-rigid, pliable, medium durometer to high durometer material, e.g., a 60 Shore A scale durometer material.

FIGS. 2(a)-2(e) show a so-called single-shot core 14 consisting of a single material, e.g., of the types listed above.

In some embodiments of the present invention, e.g., as shown in FIGS. 2(f)-2(g), the core may comprise a two-shot core 14', consisting of a more flexible top section 20, formed, e.g., from silicone (50 Shore A scale), and a more rigid inner and bottom core section 22, composed, for example, of polystyrene (65 Shore A scale).

Presently preferred materials for the top section of the two-shot core according to embodiments of the present invention, include: acrylic, natural rubber, neoprene, nitrile, polystyrene, silicon, and silicon rubber. Table 2 lists example combinations of materials for the two-shot core according to embodiments of the present invention.

TABLE 2

| Material for top section | Material for bottom core section |
| --- | --- |
| Acrylic | Foamed Polystyrene |
| Acrylic | Silicone |
| Natural Rubber | Foamed Polystyrene |

TABLE 2-continued

| Material for top section | Material for bottom core section |
|---|---|
| Natural Rubber | Silicone |
| Neoprene | Foamed Polystyrene |
| Neoprene | Silicone |
| Nitrile | Foamed Polystyrene |
| Nitrile | Silicone |
| Polystyrene | Foamed Polystyrene |
| Polystyrene | Silicone |
| Silicon Rubber | Foamed Polystyrene |

A presently preferred embodiment uses a single shot core made of a 65 Shore A scale durometer Thermoplastic Elastomer (TPE), clear in color. Other color options are also clearly within the scope of the invention.

As can be seen from FIGS. 2(b) and 2(e), the core may comprise an indented portion 15 formed around all or part of it. The indented portion may be formed by an inner ring portion or wall 13 which may be connected to the outer core by tabs 17.

In some presently preferred embodiments, the diameter of the hole 18 is 0.75 inches, the radius of curvature of the edge 19 is 1.450 inches, the thickness of the core is 0.35 inches, and the diameter of the core is 2 inches. In some embodiments the inner wall 13 is 0.2 inches thick and each of the three tabs 17 are 0.1 inches thick. As noted below, and as will be well understood by those skilled in the art, these dimensions are merely exemplary, and are not intended to limit the invention in any manner. Other dimensions are clearly within the scope of the invention.

In one implementation, the internal core of the nipple reconstruction guard is composed of a rubber compound. In a preferred exemplary implementation, the hollow opening of the core of the nipple guard is lined with a sterile gauze material.

The core section of the device contains a hollow opening that allows for the insertion of the reconstructed nipple. In some alternate embodiments, as shown, for example, in FIGS. 2(h)-2(i), the core 14" includes one or more suture anchor locations (or points or systems) 21, which enable or facilitate using sutures to secure the device (or the core section alone) directly to the nipple. The suture anchor points or locations 21 may take the form of holes formed in the core, as shown in the drawings, or some other form. Although FIGS. 2(h)-2(i) show the anchor holes 21 being formed horizontally with respect to the base of the core, those skilled in the art will realize the some or all of the anchor holes may be formed at other angles with respect to the base. In some presently preferred implementations, the core includes between two and six suture anchor points. Cores having one or more anchor locations may be formed in the same manner as the single shot or two-shot cores as described above. These embodiments are useful, e.g., for the treatment of inverted nipples. Note that in some of these embodiments, the padding section need not be attached to the core, and further, there may be no need for a separate attachment section (as described below). Thus, in embodiments in which the core include one or more suture anchor locations, the core may be used with or without either or both the padding or attachment sections.

The core section 14 of the device as illustrated in FIG. 2(e) may comprise an inner ring portion or wall 13 that is connected to an outer core via tabs 17. The indented portion 15 separates the inner ring portion 13 from the outer core.

In an embodiment of the present invention, the height of the inner ring portion 13 extends below the bottom of the core section 14 by 0.08 inches. Those of ordinary skill in the art will recognize that other height variations are possible. When used without or with a thin padding section 12 (e.g., 25 mils), these embodiments lessen the effect of the pulling forces on a reconstructed nipple originating in the local skin flap donor site area during Stage Two and Stage Three of the healing process for a newly created nipple. The inner ring portion 13 presses into the local skin flap donor site area and forms a protective barrier around a newly constructed nipple.

The Padding Section

In an assembled device, a padding section 12 lines the bottom surface of the core portion of device 10 as well as the hollow opening 18 of the device's core 14. FIGS. 3(a)-3(c) are top, side and perspective views, respectively, of a padding section 12 according to embodiments of the present invention. In some embodiments of the present invention, the padding section 12 comprises a gauze pad, preferably a sterile gauze pad, comprised, for example, of woven rayon cellulose, cotton, or a cotton/polyester blend material, or the like. In manufacture, the gauze should be trimmed to match the shape of the bottom of the core. In preferred embodiments, the thickness of the gauze should be no greater than 1/16 of an inch. In one presently preferred embodiment, the thickness of the gauze is 25 mils.

The padding section 12 includes a number of cross cuts in its center, forming a number of tabs. In preferred embodiments, there are two perpendicular cross cuts 23, 24, forming four tabs 26, 28, 30, 32. Preferably the diameter of the padding section 12 matches the diameter of the core section 14. Preferably the diameter of the cross cuts (denoted d in FIG. 3(a)) matches that of the hole 18 in the core 14 and the cross cuts in the gauze align with the hollow opening 18 in the device core 14. In this manner, in an assembled device, the tabs will be aligned with the opening 18 and, in application, a patient is able easily to push the cross-cut section of the padding into the hollow opening of the core. The width of each cross cut (denoted E in FIG. 3(a)) is preferably less than 0.03 inches. The tabs 26, 28, 30, 32 should not impinge insertion of a nipple. Those of skill in the art will immediately realize that in some embodiments of the present invention more than two cross cuts may be used, thereby creating more than four tabs. For example, four cross cuts will create eight tabs (shown as 33a-33h in FIG. 3(d)), and so forth. Two cuts provide sufficient coverage of the hollow opening 18 while, at the same time, simplifying manufacturing.

An adhesive, preferably a hypoallergenic adhesive, is preferably used to attach the padding section 12 to the bottom surface of the core section 14 of the device.

In some presently preferred embodiments, the padding component 12 is made of a non-woven, one-sided medical tape, such as Avery Dennison MED5322P. In some of these embodiments, each gauze piece is a two inch diameter circle formed to match the shape of the bottom of the corresponding core. In these embodiments, in the center of each gauze piece is a 7/8"×7/8" cross cut that will align with the hollow opening in the core. The non-woven (non-adhesive) side of the Avery Dennison MED 5322P tape is 25 mils, and is the portion that will be in direct contact with the patient's skin. The adhesive side of tape has a peel adhesion of 2.0-5.0 lb/in width and comes with a protective coating.

The cloth or padded side of the padding component 12 is the portion that will be in direct contact with patients' skin. The adhesive side is preferably covered by a removable liner so that in assembly, the manufacturer (or supplier) may remove the protective liner and apply the gauze to the core via the adhesive on the gauze piece.

In some embodiments of the present invention, the padding component 12 may comprise antibiotic soaked or treated gauze, to be used, e.g., in immediate post-operative stages.

The Attaching Portion

The attaching component 16 of the nipple reconstruction guard 10 is used to secure the device in a fixed position on the patient. FIGS. 4(*a*)-4(*c*) show various views of an attaching component 16 according to embodiments of the present invention. The attaching component 16 includes a number of tabs (four in the presently preferred embodiments—denoted 34*a*~34*d* in the drawings). These tabs are used to hold the device 10 on a patient's skin. Each of the tabs 34*a*~34*d* has a pad section that contains an adhesive so that the pads can be removably applied to a patient's skin. Preferably each pad has an individual release liner 36 (FIG. 5C) to protect the contact areas while the device is in its packaging.

In some presently preferred embodiments, the attaching component 16 is made of the same material as the padding: Avery Dennison MED5322P, which is described above. In some presently preferred embodiments, the attaching component's center portion is a circle with a 2.08" diameter (denoted D in FIG. 4(*a*)), and it has four, one inch tabs (dimension W2 in FIG. 4(*a*)) extending off of it. In some of these embodiments, the tabs comprise a 0.73" by 1.44" rectangular portion (dimensions W1 and L1, respectively in FIG. 4(*a*)) attached to the circular portion by a narrower tab about 0.27" long by 0.6" wide (dimension L2 in FIG. 4(*a*)). As noted, the dimensions are merely exemplary, and those skilled in the art will understand that other dimensions for the various parts of the tape portion may be used. In addition, while the tabs are shown as rectangles connected to the center portion by narrower segments, other shapes and connections for the tabs may be used. Other exemplary embodiments showing different type and numbers of tabs are illustrated in FIGS. 4(*d*)-4(*f*). The function of the tabs is to hold the device in place on a patient for a sufficient period of time (e.g., for five to ten hours in some preferred embodiments and for six to twelve hours in some other preferred embodiments) and those skilled in the art will realize that different types, numbers and shapes of tabs, and different composition of tape material may be used accordingly.

The center, circular portion of the attaching section may have a protective liner that has a mechanism that allows for the easy removal of the liner during assembly. In assembly, the protective liner is removed from the center of the attaching component and the attaching component is affixed to the core via the adhesive at the center of the attaching component.

Thus, in presently preferred embodiments of the present invention, the attaching section covers the top of the device and has adhesive on the bottom surface of each of its four tabs which secures the entire device to a patient's skin.

Assembly

FIGS. 5(*a*)-5(*d*) provide various views of an assembled nipple reconstruction guard 10 according to embodiments of the present invention, wherein FIG. 5(*a*)-5(*b*) are top views of an assembled device 10; FIG. 5(*c*) is a cross-sectional view of the device in FIG. 5(*a*) along the section lines A-A. As can be seen in FIG. 5(*c*), an assembled device 10 includes an attaching component (e.g., tape) covering the core. The attaching component is attached to the core by a first adhesive layer and the padding component (e.g., gauze) is attached to the core by a second adhesive layer. A removable liner 36 covers the adhesive portions of the attaching component. As shown in the drawings, raised portions 38 of the removable liner may be provided to enable easy removal of the liner.

FIGS. 5(*d*)-5(*e*) are bottom views of an assembled device 10; and FIG. 5(*f*) is a side view of the assembled device 10.

Preferably a fully assembled device 10 is packaged in and sterilized (e.g., using Gamma Sterilization, Ethylene Oxide Sterilization, or another post assembly and packaging sterilization technique) in a separate, sterilize-able, medical-grade paper or plastic wrapper. Possible packaging paper choices include but are not limited to the following: Dupont Medical Packaging's Tyvekt (spunbonded olefin); Bomarko Medical Packaging's TA100 and TA115, and Kimberly-Clark Technical Paper's Impervon™.

In some presently preferred embodiments, each fully assembled device is packaged in a non-sterile individual pouch.

In a preferred exemplary implementation, the underside of the nipple guard may be lined with a sterile gauze material. In some implementations, the nipple reconstruction guard is self-adhesive to the breast. Some alternate embodiments use a skin-tolerant adhesive directly on the bottom portion of the core, which allows the core to be attached to the area surrounding the nipple. Such configurations might be applicable, e.g., to the latter stages of the usage protocol, where the protective padding is less of a requirement. A double-sided tape may be used as the adhesive in these embodiments. In these embodiments, separate padding and attaching sections may not be necessary.

While various materials have been proposed here for the various components, those skilled in the art will realize that other materials may be used and are considered within the scope of the present invention.

While some dimensions have been provided here, by way of example, the dimensions of the nipple reconstruction guard and its various component parts may vary. Those of skill in the art will realize that different sizes will be needed and will be appropriate for different nipple sizes, and the invention is not limited by any particular dimensions. The core is hollow to allow for the insertion of the reconstructed nipple and should be sized accordingly. The padding section should preferably cover the base of the core, and should be sized accordingly. The attaching section should cover the top of the core and hold the device in place on a patient, and should be sized accordingly. Preferably the external diameter is tapered to allow for a less obtrusive look under clothing.

Use

In a specific protocol, the nipple reconstruction guard according to embodiments of the present invention is fitted around the newly constructed nipple by the surgeon (or other appropriate person) immediately following the completion of the surgical procedure. The patient is instructed to change the nipple reconstruction guard often during the recovery period, for example, one to two times per day for up to sixteen weeks or longer. Additionally, the nipple reconstruction guard may be used as part of an ongoing or longer term routine to maintain the aesthetic result.

Different embodiments of the invention may be used at different stages of treatment or for different types of treatment. For example, immediately following surgery, a stand-alone core (possibly without padding or an attaching component) may be used. The core may be sutured to the nipple, e.g., using one or more suture anchors. At a later stage of the treatment protocol, a device having a core, padding and an attaching component may be used.

The present invention enhances the aesthetic results achieved from nipple reconstruction surgery by supporting and maintaining the integrity of the reconstructed nipple.

Thus are described nipple reconstruction guards and methods of making and using same. While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

I claim:

1. A nipple reconstruction device for a nipple created from local tissue flaps comprising:
   a core component having an inner ring forming a substantially circular hollow opening therein for receiving said nipple and wherein the inner ring is sized to extend below a bottom of the core component and wherein the core component further comprises an outer ring attached to the inner ring by one or more tabs;
   a padding component attached to the bottom of the core without covering the circular hollow opening of the core component; and
   an attaching component for holding said nipple reconstruction device in place over said nipple.

2. The device in claim 1 wherein the inner ring of the core component extends below a bottom of the outer ring of the core component by 0.08 inches.

3. The device in claim 1 wherein the diameter of the circular hollow opening is about 0.75 inches.

4. The device in claim 1 wherein the thickness of the inner ring of the core component is about 0.2 inches.

5. The device in claim 1 wherein the diameter of the bottom of the core component is about 2 inches.

6. The device in claim 1 wherein the core component is a 65 Shore A scale durometer material.

7. The device in claim 6 wherein the core component is comprised of Thermoplastic Elastomer.

8. The device in claim 1 wherein the padding component is a one-sided medical tape having a thickness of about 25 mils.

9. The device in claim 1 wherein the attaching component comprises a plurality of tabs for holding the device in place over the reconstructed nipple.

10. The device in claim 9 wherein the attaching component comprises an adhesive having at least four tabs.

11. The device in claim 9 wherein the tabs contain an adhesive.

12. A nipple reconstruction device for a nipple created from local tissue flaps comprising:
    a core component having an inner ring forming a substantially circular hollow opening therein for receiving said nipple and wherein the inner ring is sized to extend below a bottom of the core component, and wherein the core component further comprises an outer ring attached to the inner ring by one or more tabs, and wherein the inner ring of the core component extends below a bottom of the outer ring of the core component by about 0.08 inches;
    a padding component attached to the bottom of the core without covering the circular hollow opening of the core component; and
    an attaching component for holding said nipple reconstruction device in place over said nipple, wherein the attaching component comprises an adhesive having at least four tabs for holding the device in place over the reconstructed nipple.

13. The device in claim 12 wherein the diameter of the circular hollow opening is about 0.75 inches.

14. The device in claim 12 wherein the thickness of the inner ring of the core component is about 0.2 inches.

15. The device in claim 12 wherein the diameter of the bottom of the core component is about 2 inches.

16. The device in claim 12 wherein the core component is a 65 Shore A scale durometer material.

17. The device in claim 16 wherein the core component is comprised of Thermoplastic Elastomer.

18. The device in claim 12 wherein the padding component is a one-sided medical tape having a thickness of about 25 mils.

19. A nipple reconstruction device for a nipple created from local tissue flaps comprising:
    a core component having an inner ring forming a substantially circular hollow opening therein for receiving said nipple and wherein the inner ring is sized to extend below a bottom of the core component, and wherein the core component further comprises an outer ring attached to the inner ring by one or more tabs, and wherein the inner ring of the core component extends below a bottom of the outer ring of the core component by about 0.08 inches;
    a padding component attached to the bottom of the core without covering the circular hollow opening of the core component; and
    an attaching component for holding said nipple reconstruction device in place over said nipple, wherein the attaching component comprises an adhesive having at least four tabs for holding the device in place over the reconstructed nipple,
    wherein the diameter of the circular hollow opening is about 0.75 inches, and
    wherein the thickness of the inner ring of the core component is about 0.2 inches, and
    wherein the diameter of the bottom of the core component is about 2 inches; and
    wherein the padding component is a one-sided medical tape having a thickness of about 25 mils.

20. The device in claim 19 wherein the core component is a 65 Shore A scale durometer material.

* * * * *